(12) United States Patent
Bruno et al.

(10) Patent No.: US 11,246,607 B2
(45) Date of Patent: Feb. 15, 2022

(54) LASER STERNOTOME

(71) Applicant: ADVANCED OSTEOTOMY TOOLS—AOT AG, Basel (CH)

(72) Inventors: Alfredo E. Bruno, Biel-Benken (CH);
Philippe C. Cattin, Windisch (CH)

(73) Assignee: ADVANCED OSTEOTOMY TOOLS—AOT AG, Basel (CH)

( * ) Notice: Subject to any disclaimer, the term of this patent is extended or adjusted under 35 U.S.C. 154(b) by 30 days.

(21) Appl. No.: 16/312,933

(22) PCT Filed: Jun. 22, 2017

(86) PCT No.: PCT/EP2017/065372
§ 371 (c)(1),
(2) Date: Dec. 21, 2018

(87) PCT Pub. No.: WO2017/220719
PCT Pub. Date: Dec. 28, 2017

(65) Prior Publication Data
US 2019/0159789 A1 May 30, 2019

(30) Foreign Application Priority Data

Jun. 22, 2016 (EP) ..................................... 16175604

(51) Int. Cl.
*A61B 17/16* (2006.01)
*A61B 18/22* (2006.01)
(Continued)

(52) U.S. Cl.
CPC .......... *A61B 17/1691* (2013.01); *A61B 18/20* (2013.01); *A61B 18/22* (2013.01); *A61B 17/56* (2013.01); *A61B 2018/00333* (2013.01)

(58) Field of Classification Search
CPC . A61B 17/15; A61B 17/1691; A61B 17/1789; A61B 17/56; A61B 17/8076;
(Continued)

(56) References Cited

U.S. PATENT DOCUMENTS 5,320,111 A * 6/1994 Livingston ......... A61B 17/3403
378/206
6,044,291 A 3/2000 Röckseisen
(Continued)

FOREIGN PATENT DOCUMENTS

EP 2 821 023 A1 1/2015
JP 2011519659 A 7/2011
(Continued)

OTHER PUBLICATIONS

International Search Report dated Aug. 1, 2017 in corresponding International Application No. PCT/EP2017/065372.

*Primary Examiner* — Carl H Layno
*Assistant Examiner* — Jane C Kalinock
(74) *Attorney, Agent, or Firm* — Medler Ferro Woodhouse & Mills

(57) ABSTRACT

A cutting device for cutting a sternum of a patient comprises a laser source, a beam adjusting structure, a support and a correction arrangement. The laser source is adapted to generate a cut laser beam. The beam adjusting structure is arranged for directing the laser beam along a predefined cut geometry at the sternum. The support carries the laser source. The support has a mounting structure adapted to be fixed to a rib cage of the patient such that the laser source is in a predefined position with respect to the sternum. The correction arrangement is adapted to automatically identify a movement of the laser source relative to the sternum causing the cut laser beam to deviate from the predefined cut geometry and adjust the position of the laser source relative
(Continued)

to the sternum to correct the deviation of the cut laser beam with respect to the predefined cut geometry.

17 Claims, 5 Drawing Sheets

(51) Int. Cl.
*A61B 18/20* (2006.01)
*A61B 18/00* (2006.01)
*A61B 17/56* (2006.01)

(58) Field of Classification Search
CPC ....... A61B 17/823; A61B 18/20; A61B 18/22; A61B 2018/00333; A61B 2018/00565; A61B 2018/00577; A61B 2018/00601; A61B 2018/00738; A61B 2018/205547; A61B 90/50; A61B 2017/320052; A61B 2017/320093; A61N 5/1037; A61N 2005/0642
USPC .......................................................... 606/13
See application file for complete search history.

(56) References Cited

U.S. PATENT DOCUMENTS

| | | | |
|---|---|---|---|
| 6,159,168 A * | 12/2000 | Warner | A61B 5/103 600/594 |
| 6,283,127 B1 | 9/2001 | Sterman et al. | |
| 2008/0033410 A1* | 2/2008 | Rastegar | A61B 18/20 606/9 |
| 2011/0082459 A1* | 4/2011 | Aravot | A61B 17/1789 606/79 |
| 2012/0220992 A1* | 8/2012 | Bruno | A61B 34/30 606/13 |
| 2016/0067006 A1* | 3/2016 | Steinberg | A61F 2/30742 606/130 |
| 2017/0258532 A1* | 9/2017 | Shalayev | A61B 17/1626 |

FOREIGN PATENT DOCUMENTS

| | | |
|---|---|---|
| WO | 2008136001 A2 | 11/2008 |
| WO | 2015000823 A1 | 1/2015 |

* cited by examiner

LASER STERNOTOME

CROSS-REFERENCE TO RELATED APPLICATION(S)

This application is a national phase entry under 35 U.S.C. 371 of PCT Appl. PCT/EP2017/065372, filed Jun. 22, 2017, which claims priority to EP Appl. No. 16175604.4, filed Jun. 22, 2016, the entire contents of which are incorporated herein in their entirety.

TECHNICAL FIELD

The present invention relates to a cutting device comprising a laser source, a beam adjusting structure and a support. The laser source is adapted to generate a cut laser beam. The beam adjusting structure is adapted for directing the cut laser beam generated by the laser source along a predefined cut geometry at a sternum. The support carries the laser source. Such devices can be used for cutting a sternum of a patient in various medical applications.

BACKGROUND ART

In many medical applications human or animal bones are cut or drilled for various purposes. For example, for correcting the shape of a bone it is known to apply one or plural cuts to a bone and to reshape the bone along the cuts. For the removal of tumors in bone, or, for replacing a tooth it is common practice to drill a hole in the jaw bone and to provide an implant into the drilled hole as an artificial tooth root. For applying such cuts many types of instruments or tools are used depending on the specific circumstances of the cuts.

More particularly, in various medical or surgical applications the sternum of a human being is cut. For example, for gaining access to the thoracic organs, e.g. for accessing the heart in cardiothoracic surgery, the sternum is cut apart such that the rib cage can be opened. Thereby, a vertical inline incision is typically made along the sternum after which the sternum is divided or cracked. Since the organs and other tissue inside the interior of the rib cage are highly sensitive and of crucial importance for the health of the patient, the sternum has to be precisely and carefully divided. This is particularly difficult since the sternum is a comparably thick and strong bone structure and, vital organs such as the heart and lung are in contact with it.

As instruments for cutting sterna it is widespread to use mechanical tools such as conventional or oscillating saws, piezoelectric osteotomes or the like. The principal generally underlying the cutting of bones by means of such osteotomic instruments is essentially the same for all different types of instruments. This is, the respective instrument puts mechanical stress onto the bone surface until a surface hardness is exceeded and the instrument breaks into the bone.

In addition to conventional mechanical osteotomic instruments, in recent years there have alternative bone cutting instruments been developed which allow for a comparably precise and gentle cutting also of thick and strong bones such as the sternum. For example, in WO 2011/035792 A1 a computer assisted and robot guided laser osteotome is described which makes highly precise and gentle cutting of bones possible even if the bones are comparably thick and strong. Said laser osteotome includes a laser head mounted to a robot arm. While the laser head provides a laser beam, the robot arm guides the laser head along a predefined cutting geometry at the bone to be cut. Thereby, the robot arm allows for a highly precise and comparably fast movement of the laser head in all directions and orientations. The laser beam then hits the bone and continuously ablates the bone tissue until the predefined cutting geometry is generated. Cutting by laser has many advantages compared to conventional mechanical tools such as a comparably quick reaction, e.g. for stopping the intervention in case of an emergency, comparably little collateral damage and a comparably high precision particularly when involving complex cutting geometries. Of particular importance is the fact that the surface of the bone when properly cut using laser light is not damaged by the friction of a mechanical tool exposing the bone to high temperatures, mechanical stress and blocking the porous surface with the generated debris. The laser osteotome further includes assisting arrangements like a spray to cool and humidify the tissue around the laser beam-bone contact area, a debris nozzle for removing debris generated by the cutting process and an auto-tracking mechanism. In contrast to known mechanical methods for cutting bone, the surface of the laser cut bones can retain the original trabecular structure, which does not block the flow of blood which can be important to start the healing process.

Even though known laser osteotomes of the kind mentioned above are rather universal in terms of medical indications allowing for a sophisticated cutting of all kind of bones including sterna such osteotomes and particularly its robot arms are comparably large. Furthermore, they usually are comparably costly such that many facilities where such an osteotome could be used cannot afford it.

Therefore, there is a need for a comparably cost efficient and handy device allowing to precisely, quickly and reliantly cut the sternum of a patient.

DISCLOSURE OF THE INVENTION

According to the invention this need is settled by a device as it is defined by the features of independent claim 1. Preferred embodiments are subject of the dependent claims.

In particular, the invention is a cutting device for cutting a sternum of a patient. The cutting device comprises a laser source adapted to generate a cut laser beam, a beam adjusting structure for directing the cut laser beam generated by the laser source along a predefined cut geometry at the sternum, and a support carrying the laser source. The support has a mounting structure to be fixed to a rib cage of the patient such that the laser source is in a predefined position with respect to the sternum.

The term "sternum" or breastbone as used herein relates to a long flat bone, which is shaped like a necktie, and is located in the center of the chest. It connects to the ribs via cartilage, forming the front of the rib cage, and thus helps to protect the heart, lungs and major blood vessels. The sternum can be sectioned in three regions, i.e. from top down, the manubrium, the body and the xiphoid process. Thereby, the term "bone" can refer to natural human or animal bones as well as to artificial bones or bone replacements.

The term "laser source" as used herein can relate to a complete laser device or particularly to the single portion thereof where the laser beam exits. For example, the laser source can be a laser head of the laser device or an optical component at the output end of an optical fiber or waveguide such as a hollow fiber where the light from the laser device emerges collimated or anything else from which the cut laser beam is emitted by the laser device. Typically, laser devices comprise plural portions such as a fixed base station with power means, controls, programming elements and the like. Often they additionally comprise a laser head or hand piece which is flexibly movable in relation to the base station, e.g., using an articulated arm having a series of mirrors to stir the laser beam. The laser beam usually exits the laser device at a portion of the hand piece or laser head, e.g. an optical portion or focusing optics, such that in accordance with the present disclosure this portion can be the laser source.

The term "osteotomic geometry" as used herein relates to any geometry defined on the sternum or bone for specifying the cut to be applied. Such osteotomic geometry can be, for example, a straight or curved line along which the bone is to be cut or a more complex geometry defining a target fashion of intervening the bone. The osteotomic geometry typically is predefined in a preoperative planning step. It can be predefined based on gathered data of the bone such as, e.g., computer tomography data.

The osteotomic geometry can be predefined by means of a computer. It can also be defined directly on the sternum without the need of preoperative data from, e.g., a computer tomography scan or the like. For example, this can be performed using an optical tracking camera and an optical pointer tool used by the surgeon to point at the starting and end points of the desired cut. Such selection can then be transmitted to a laser sternotome control unit. Furthermore, for this direct definition of the osteotomic geometry a software program could then prompt the surgeon or operator for the desired cutting geometry and its parameters such as a sinusoidal cut where the operator could choose the number of periods within the starting and end points of the cut. In addition, the software could also prompt for an incident angle of the laser beam that is different from the default which can be essentially perpendicular to the sternum.

A possible option for precisely directing the cut laser beam is that the beam adjusting structure moves the laser source into a predefined position and orientation. Thereby, the term "predefined position and orientation" can relate to any predefined position and predefined orientation allowing the laser source to deliver a suitable beam to the sternum in order to ablate it along the predefined cut geometry. The predefined position and orientation can, thus, correlate to the predefined cut geometry. Thereby, the position can be predefined in vicinity of the sternum such that a laser beam generated by the laser source can unhindered reach the sternum. The orientation of the laser source can be predefined such that a cut laser beam generated by the laser source can directly reach the cut surface at a preferred bone striking angle. Such predefined bone striking angle can for example be an essentially right angle.

Another possible option for precisely directing the cut laser beam is that the laser beam emerging from the laser source, a mirror articulated arm or the output collimator of an optical fiber is directed to the sternum by means of a two-dimensional (XY) or three-dimensional stage (XYZ) translation stage with linear motors by means of flat or curved mirrors mounted at a fix position or in scanners.

In medical applications where the sternum is to be cut apart, it can be advantageous that the cut laser beam is a pulsed laser beam. Thereby, the laser source can be a solid-state Erbium laser source or, particularly, a solid-state Erbium-doped Yttrium Aluminium Garnet laser source. The pulses of such a laser beam can be sub-microsecond pulses. The cut laser beam can, thus, be generated by a solid-state Erbium laser device such as a solid-state Erbium laser source described below. Such devices and pulsed laser beams allow for a precise and efficient ablation of the bone tissue of the sternum with no or minimal collateral damages on the bone structure of the sternum. Beside the various types of solid-state Erbium lasers such as a diode laser or flash lamp pumped lasers, any other pulsed laser beam such as solid-state Holmium or $CO_2$ gas laser beam that are known to also ablate bone tissue can be used.

The cut laser beam can have a wavelength in a range of about 2,900 nanometer (nm) to about 3,000 nm or, particularly, a wavelength of about 2,940 nm. Such wavelength can particularly be suitable for being delivered to bone tissue. The laser pulses can have a time width in the range of 1 pico-second to about 100 milli seconds or, particularly, a time-width of 100 micro-seconds to about 2 milli-seconds. Selection of the laser and adjustment to correct properties can be crucial for efficiently removing bone tissue and, thus, for an efficient ablation of the bone tissue along the cut geometry.

Preferably, the cutting device further comprises a correction arrangement which is adapted to automatically identify a movement of the laser source relative to the sternum causing the cut laser beam of the laser source to deviate from the predefined cut geometry. The "term movement of the laser source relative to the sternum" as used herein includes a movement of the laser source as well as a movement of the sternum as well as simultaneous movements of both as long as a relative movement between the two is involved which leads to the deviation from the predefined cut geometry. The correction arrangement preferably further is adapted to automatically adjust the position of the laser source relative to the sternum to correct the deviation of the cut laser beam of the laser source with respect to the predefined cut geometry. Thereby, in a preferred embodiment, the correction arrangement is adapted to stop the generation of the cut laser beam when the deviation from the predefined cut geometry is identified and to resume the generation of the cut laser beam when the deviation is corrected.

For identification purposes, the correction arrangement preferably comprises a sensor adapted to provide a spatial signal related to the position of the cut laser beam and the sternum relative to each other. Such a sensor can be or comprise a distance laser source adapted to provide and conceive a distance laser beam to the sternum, an ultrasonic sensor adapted to provide and conceive an acoustic wave to the sternum, a camera adapted to monitor the sternum, an infrared sensor adapted to provide and conceive infrared light to the sternum and the like.

The correction arrangement can further have a computing device or a software application executed on a computing device. Such a computing device can be embodied to automatically evaluate signals or information in connection with an automatically identified movement of the laser source relative to the sternum. In particular, it can be adapted to evaluate a signal provided by the mentioned sensor.

For adjusting the position of the laser source relative to the sternum in order to correct a deviation of the cut laser beam of the laser source with respect to the predefined cut geometry the correction arrangement can be connected to the beam adjusting structure. In particular, it can provide commands to the beam adjusting structure in order to move the laser source or otherwise adapt the cut laser beam for correcting the identified deviation. Thereby, the commands can be generated and provided by the computing device.

In use, after preoperative planning where, beyond others, the cut geometry is predefined, the cutting device is mounted to the rib cage of the patient via the mounting structure of its support. Thereby, the laser source is in a well-defined position in relation to the sternum. Particularly since the patient is still breathing while his sternum is cut, the ribs are constantly moving. Since the cutting device is attached directly to the patient by means of the mounting structure, it moves together with the rib cage such that it can be achieved that no further motion compensation is needed. Thus, the cutting device according to the invention, as a comparably handy device, allows for a precise and reliant cutting of the sternum of the patient.

However, in an embodiment of the invention, the additional correction arrangement constantly and automatically identifies deviations of this well-defined position of the laser head and automatically corrects the identified deviations. As mentioned such correction can be embodied by moving the laser source and/or by reshaping the cut laser beam. This can allow for providing enhanced cutting accuracy particularly in situations where relative movements between the cutting device and the sternum might occur or where such relative movements are comparably large.

Preferably, the support comprises a carrier element and the correction arrangement is adapted to automatically identify a movement of the carrier element relative to the sternum. In particular, the carrier element can be fixedly connected to the mounting structure. By monitoring the carrier element with regard to movements relative to the sternum the correction arrangement allows for efficiently correcting a deviation of the laser source relative to the sternum.

Thereby, the support preferably comprises a laser mount to which the laser source is fixedly mounted and the laser mount preferably is movably connected to the carrier element. Since the laser source can be in motion in relation to the sternum in order to correctly provide the cut laser beam to the sternum it can be difficult to distinguish between a portion of a movement of the laser source which is necessary, i.e. for cutting the sternum, and another portion of the movement of the laser source which is unintentionally, e.g. by a breathing motion. By providing the laser mount as described these two portions of the movements of the laser source can efficiently be separated. In particular, by monitoring the carrier element the correction arrangement only identifies the unintentional portion of a movement of the laser source whereas the necessary portion is not noticed or considered by the correction arrangement.

The cutting device preferably comprises a drive unit adapted to move the laser source relative to the carrier element. In particular, the drive unit can be adapted to move the cut laser beam along the cut geometry of the sternum. With such a drive unit the cut laser beam can automatically or semi-automatically be moved along the cut geometry. For example, the drive unit can be programmable such that in a preoperative planning step it can be appropriately adjusted. The drive unit allows for increasing efficiency and accuracy when ablating bone tissue for cutting the sternum. Also, the correction arrangement can manipulate the drive unit in order to correct an identified deviation. For example, the correction arrangement can be connected to the drive unit and provide control signals to it. Like this, deviations between the laser source and the sternum can be efficiently compensated.

Thereby, the drive unit preferably comprises a linear motor adapted to move the laser source relative to the carrier element. Such a linear motor allows for quickly and precisely moving the laser source. Like this, the cut laser beam generated by the laser source can be efficiently guided along the cut geometry of the sternum by moving the laser source or parts thereof. Also, correction of the movement of the laser source can efficiently be provided by such a linear motor. In particular, as a safety feature, whenever the position of the sternum requires a correction the cutting device might temporarily stop laser beam generation until the spatial corrections are achieved.

Alternatively or additionally, the drive unit preferably comprises a beam director adapted to adjust a direction into which the cut laser beam generated by the laser source is provided. Thereby, the beam director preferably comprises a hinge motor or mirror mounted in a hinge motor or a scanner of any type adapted to tilt the laser source relative to the carrier element. Alternatively or additionally the beam director preferably comprises an adjustable optics adapted to redirect the cut laser beam generated by the laser source. The adjustable optics can comprise a mirror deflecting the cut laser beam provided by the laser source, wherein the mirror can be rotated around an axis such that the cut laser beam can be radially provided around 360°. Such hinge motor and/or optics allow for sophisticatedly providing the cut laser beam in any desired manner. This allows for applying, comparably complex cut geometries and for precisely correcting identified deviations.

The mounting structure of the support is embodied to be connected to the sternum in a fixed manner. For example, it can have clipping or clamping means allowing it to be releasably but fixedly mounted to the sternum. Also, it can comprise screws and screw recesses for being screwed to the ribs. Preferably, the mounting structure of the support comprises plural legs each having a foot shaped to be fixed to one of the ribs of the rib cage of the patient. Like this, an efficient fixation and definition of the position of the laser head relative to the sternum is possible.

Alternatively, the mounting structure of the support preferably comprises a hollow post shaped to be fixed to plural ribs of the rib cage and positioned such that the cut laser beam of the laser source is passing through its hollow interior. Such a post allows for precisely positioning the cutting device relative to the sternum and at the same time to cover the laser beam and to shield debris generated by the cutting of the sternum.

Preferably, the mounting structure of the support comprises a belt or plural belts adapted to fix the mounting structure to the rib cage. Such a belt can be applied in addition to other mounting means or also as an alternative thereto. A belt allows for a fast, gentle and easy fixation of the cutting device to the rib cage. It also allows for pre-fixing the cutting device such that the final fixing, e.g. by screws, can conveniently be applied if necessary.

In use, the cutting device ablates the sternum at or along the cut geometry. During laser ablation debris is generated wherein by means of the cut laser beam the debris generated travels away from the bone at comparably high velocities such as, e.g. at about 2,000 m/s. From the perspective of the bone the ablation by the cut laser beam can be referred to as debris free because the trabecular structure is not contaminated with debris. Also, it can be referred to as cold (photo or laser) ablation because no melting of the bone surface is observed using the here described device and method. However, to evacuate the debris generated when cutting the sternum of the patient, the cutting device preferably comprises a suction element or a debris extraction unit adapted to remove debris generated by the cut laser beam hitting the sternum. Such suction or debris extraction can help to keep the cut geometry and the room around it clean.

For cooling and hydrating the sternum where the cut laser beam is applied the cutting device can comprise a spray nozzle or a nozzle array. Thereby, multi-fluid nozzles can be particularly efficient. The cooling fluid can be a sterile sodium chloride. It allows for minimizing heat transfer from the cut laser beam-bone tissue contact area to other sections of the bone. Thus, collateral damages of the bone tissue can be prevented or minimized.

Preferably, the cutting device comprises a depth detecting unit adapted to detect a depth of an ablation applied to the sternum. Such a unit allows for precisely ablating bone tissue up to a desired depth. Thereby, variations in the nature of the bone tissue can be considered. For example, the depth detecting unit can continuously provide information about the depth of the ablated bone tissue to a central control unit which adjusts the cutting laser beam and/or the drive in response thereto. This allows for an efficient and safe cutting of the sternum.

Preferably, the cutting device comprises an auto-focusing arrangement adapted to automatically adjust a focus of the cut laser beam in relation to the cut geometry of the sternum. Such auto-focusing arrangement allows for continuously adapting the focus with advancing ablation. In an advantageous embodiment the auto focusing arrangement is combined with the depth detecting unit mentioned above. Thereby, the auto-focusing arrangement preferably is adapted to adjust the focus of the cut laser beam in accordance with the depth detected by the depth detecting unit. In this way, the focal point of the cut laser beam can automatically be adjusted in order to ensure that a predefined cut laser beam intensity hits the sternum at the cut geometry. Thereby, the focus can be continuously adjusted in accordance with the respective depth of the ablated bone tissue. The auto-focusing arrangement can comprise a parabolic mirror. Also, it can be the laser source of the cutting device, e.g., by being the element from which the cut laser beam is emitted.

Preferably, the cutting device comprises a depth control unit arranged to stop the laser source generating laser the cut laser beam when the sternum is cut to a predefined extent. Considering that the Sternum is separated from the heart and lung by a very thin membrane only it can be paramount importance to be able to control the cutting depth along the entire cut geometry. In particular, it can be important to control the cutting depth and profile to be able to stop the cut laser beam generation once the sternum is completely cut or, just before this point leaving a very thin residual bone in such way that the surgeon can easily split it at the end once the entire cut geometry is provided. Thus, the term "predefined extent" in connection with the cut can relate to a depth corresponding to the depth of the sternum or essentially the depth of the sternum.

There are some preferred suitable ways to implement such depth control units. In one embodiment the depth control unit is a laser based optical coherence tomography (OCT) device. By using such OCT device and an additional laser beam which can be propagated in a coaxial mode with the cut laser beam the depth of the cut can be controlled in real time, e.g., immediately after each laser shot.

In another embodiment the depth control unit is a laser based photo-acoustic spectroscopy sensor. The use of such a laser photo-acoustic spectroscopy (PAS) sensor can allow to determine if the last shot had encountered a hard or a soft tissue. Thus, conclusions can be efficiently drawn if the sternum is completely cut or not.

Generally, when cutting the sternum or after each laser pulse there is debris flying away from the cut. This debris can be exposed to high temperature implying that any pathogen which could be present in the cutting path cannot survive. However, it might be of interest to capture the debris with a debris elimination unit of the cutting device. This unit can, e.g., comprise a suction arrangement which can be positioned in the vicinity of the cut. Alternatively, this could be done with a separate instrument.

BRIEF DESCRIPTION OF THE DRAWINGS

The cutting device according to the invention is described in more detail herein below by way of exemplary embodiments and with reference to the attached schematic drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
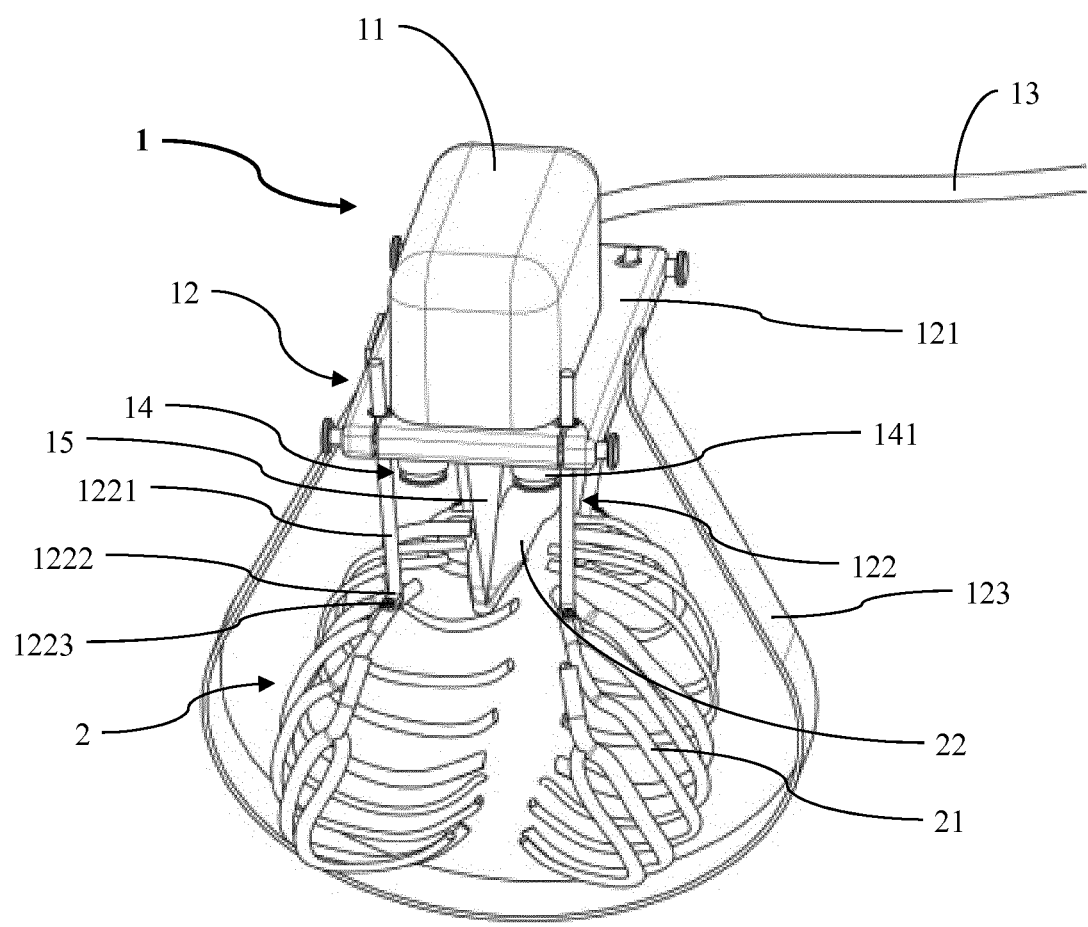
FIG. 1 shows a perspective view of a portion of a first embodiment of a cutting device according to the invention mounted to a rib cage.

FIG. 1 shows an embodiment of a cutting device 1 according to the invention. The cutting device 1 comprises a support 12 carrying a housing 11 and correction arrangement 14. A laser source (not visible in FIG. 1) is arranged in the housing 11 and carried by the support 12. It is adapted to generate or provide a cut laser beam 15.

The support 12 has a mounting structure with four legs 122. Each of the legs has a post 1221 and a foot 1222 adapted to be fixed to one of the ribs 21 of a rib cage 2 of a patient by means of a screw 1223. In particular, the feet 1222 are equipped with a concave lower surface being shaped to receive one of the ribs 21 of the rib cage 2. For fixing the mounting structure to the rib cage 2, at least while the feet 1222 of the legs 122 are screwed to the ribs 21, the support 12 comprises a belt 123. The belt 123 is arranged around the rib cage 2 and tightened in a common fashion. When being fixed to the rib cage 2 the cutting device 1 is positioned above a sternum 22 of the rib cage 2.

The support 12 further has a carrier plate 121 as carrier element which is connected to the four legs 122. The connection between the legs 122 and the carrier plate 121 is adjustable such that a distance between the carrier plate 121 and the sternum 22 can be varied. Once adjusted, the legs 122 and the carrier plate 121 are firmly connected such that the position and orientation of the carrier plate 121 is predefined with respect to the sternum 22 as long as the sternum 22 and the ribs 21 are not moved in relation to each other.

The cutting device 1 further comprises a correction arrangement 14 having one or plural cameras 141 as sensors mounted to the carrier plate 121 of the support 12. The cameras 141 are directed towards the sternum 22 or, more particularly, to an area of the sternum 22 where it is hit by the cut laser beam 15. The cameras 141 are adapted to provide a spatial signal related to the position of the carrier plate 121 and, thus, the laser source (not visible in FIG. 1) and the cut laser beam 15 relative to the sternum 22. The correction arrangement 14 further comprises a computing unit implemented in an electronic unit 17 (not shown in FIG. 1) which receives and evaluates the spatial signal of the cameras 141. When identifying a deviation of the position of the carrier plate 121 relative to the sternum 22, the computing unit of the correction arrangement 14 provides control signals to a drive unit 19 (not visible in FIG. 1) for correcting the deviation. For communicating with the computing device 17 and for other interactions, the cutting device 1 comprises a media wiring 13.

Figure 2:
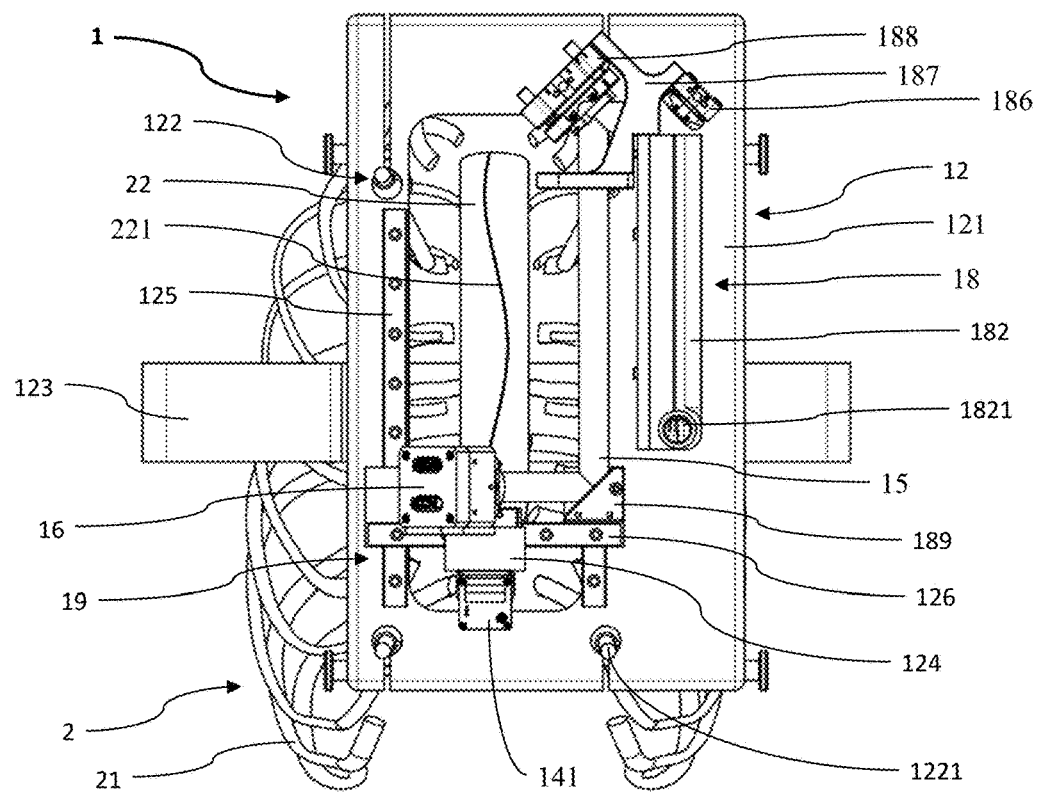
FIG. 2 shows a top view of the cutting device of FIG. 1 wherein a housing is removed.

In FIG. 2 the cutting device is shown without the housing 11 and media wiring 13. Thereby, it can be seen that a laser applicator 182 of a laser device 18 is mounted onto the support plate 121. The laser applicator 182 has a fiber connector 1821 to which an optical fiber of the media wiring 13 can be connected. The laser applicator 182 has an exit out of which the cut laser beam 15 light is emitted. In FIG. 2 the laser applicator 182 provides the cut laser beam 15 light in an upward direction.

The laser device 18 further has a first redirecting mirror 186 which deflects the cut laser beam 15 by 90° to the left through a lens unit 187. By the lens unit 187 the cut laser beam 15 is widened. Left hand side of the lens unit 187 the laser device comprises a second redirecting mirror 188 which deflects the widened cut laser beam 15 by 90° in a downward direction. Thereby, the cut laser beam 15 travels along the laser applicator 182 until it hits a third redirecting mirror 189 of the laser device 18. The third redirecting mirror 189 deflects the widened cut laser beam 15 again by 90° to the left where it is directed to a parabolic mirror member 16.

The parabolic mirror member 16 is adjustable in various manner. Particularly, it has a parabolic mirror the cone or geometry of which can be adjusted. The widened cut laser beam 15 hits the parabolic mirror of the parabolic mirror member 16 which on one hand redirects it towards the sternum 22 and on the other hand focusses the cut laser beam 15. Thus, the parabolic mirror member 16 forms a laser source of the cutting device 1. By adjusting the cone of the parabolic mirror the focus or geometry of the cut laser beam 15 can be adapted. The parabolic mirror member 16 is controlled to automatically focus the cut laser beam 15 at the sternum 22. Thus, it additionally forms an auto-focusing arrangement of the cutting device 1 which also allows for precisely adjusting the intensity of the cut laser beam 15 at the cut geometry 221. Like this, efficiently ablation of bone tissue is possible at the sternum 22. Furthermore, adjusting the parabolic mirror member 16 defines a direction in which the cut laser beam is emitted by the cutting device 1. Thereby, the parabolic mirror member 16 is controlled to apply a predefined cut geometry 221 to the sternum 22.

The parabolic mirror member 16 is fixed on a laser mount 124 which is movably connected to the carrier plate 121. The laser mount 124 is connected to a horizontal x-rail 126 and a vertical y-rail 125. Together the parabolic mirror member 16, the laser mount 124, the x-rail 126 and the y-rail 125 form a beam adjusting structure or beam director of a drive unit 19 of the laser device 1. The drive unit 19 further has a hinge motor adapted to tilt the laser mount 124 in order to adjust the direction into which the cut laser beam 15 is provided form the parabolic mirror member 16. It further comprises linear motors which move the laser mount 124 along the x-rail 126 and the y-rail 125. For precisely cutting the sternum 22 along the predefined cut geometry 221 the parabolic mirror member 16 is adjusted. Once a limit of a suitable range of adjustment of the parabolic mirror member 16 is reached cut laser beam 15 generation is stopped and the parabolic mirror member 16 is relocated by moving and tilting it. When being properly relocated the cutting the sternum 22 along the cut geometry 221 is continued.

Figure 3:
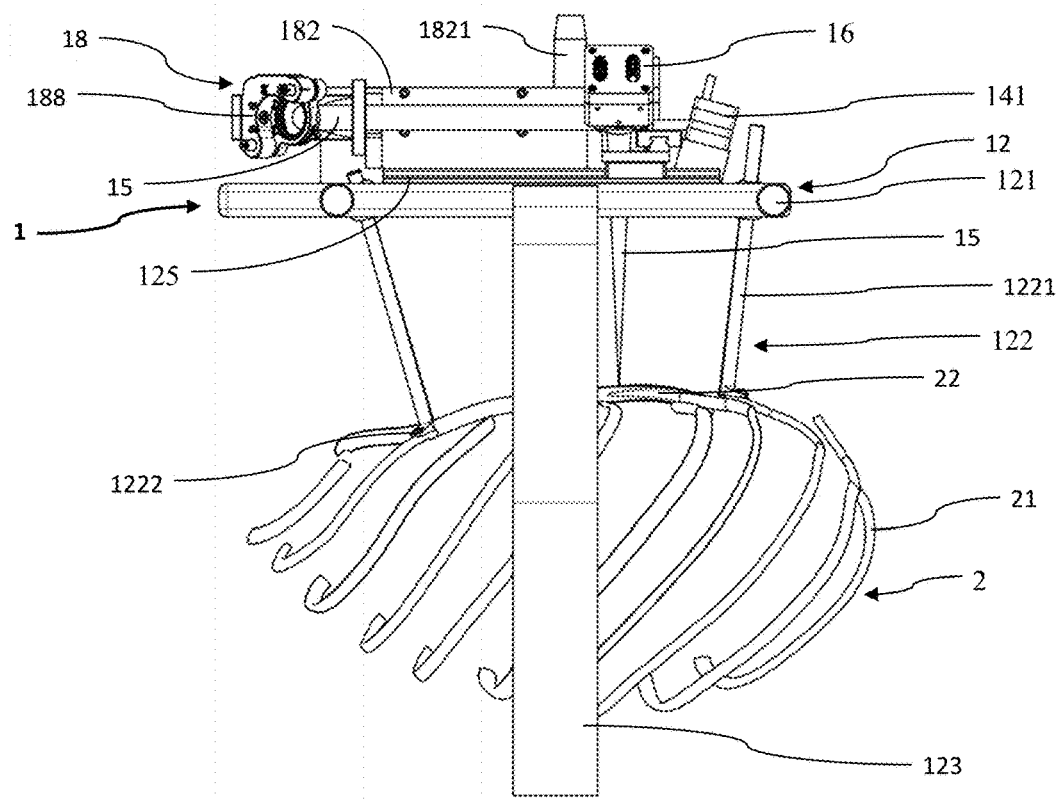
FIG. 3 shows a side view of the cutting device of FIG. 1 wherein the housing is removed.

FIG. 3 shows the cutting device 1 from the side. Thereby, it can be seen that the camera 141 is directed towards the sternum 22 or, more particularly, to the section of the sternum where the cut laser beam 15 hits the tissue. Also it can be seen that the parabolic mirror member 16 has two sockets as an interface to which a control and/or data transmission can be connected.

Figure 4:
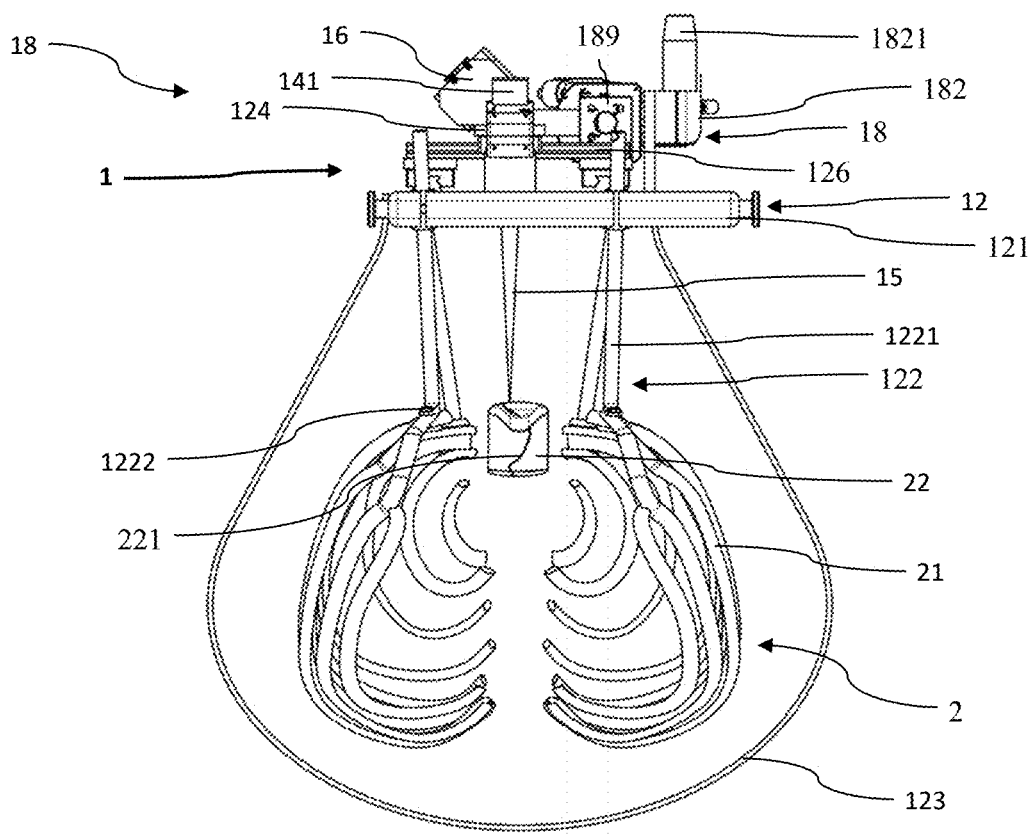
FIG. 4 shows a front view of the cutting device of FIG. 1 wherein the housing is removed.

FIG. 4 shows the cutting device from a front. The parabolic mirror member 16 is tilted to the left side which allows for efficiently receiving the widened cut laser beam 15 from the third redirecting mirror 189. The cutting device 1 further comprises a suction nose of a debris extraction unit (not shown in the Figs.). The suction nose is adapted to evacuate debris generated by the cut laser beam 15 hitting the sternum 22.

Figure 5:
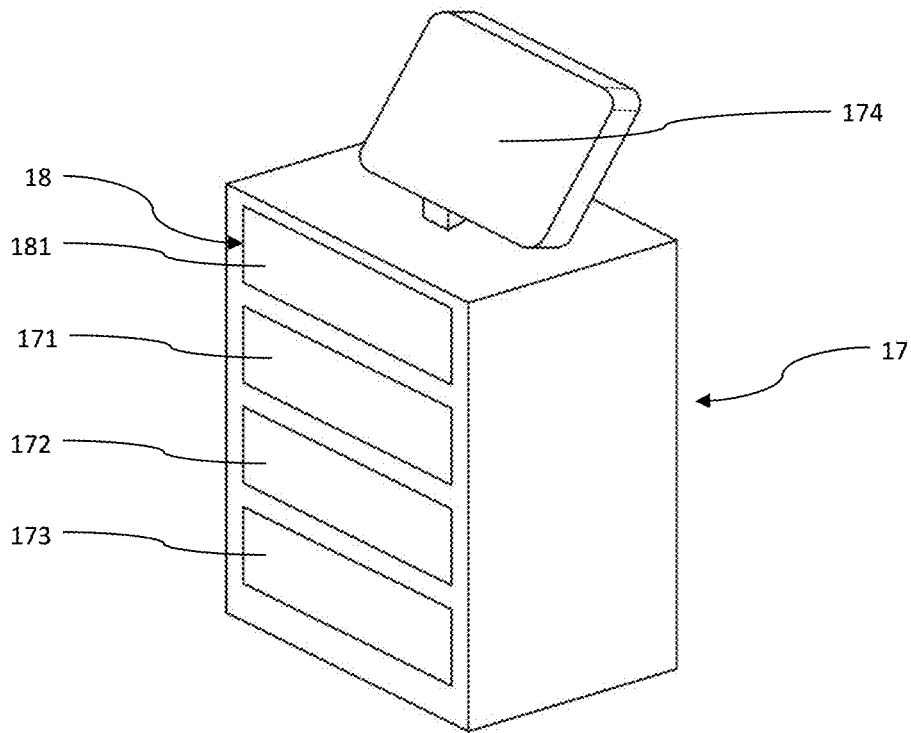
FIG. 5 shows a perspective view of an electronic unit of the cutting device of FIG. 1.

In FIG. 5 an electronic unit 17 of the cutting device 1 is shown. It is connected to the housing 11 and the other respective components of the cutting device 1 via the media wiring 13. The electronic unit 17 comprises a gas and liquid control 171, a depth detecting unit 172, a processing unit 173 including the computing unit of the correction arrangement and a display 174. Furthermore, it is equipped with a solid-state Erbium-doped Yttrium Aluminium Garnet (Er:YAG) laser 181 of the laser device 18 which laser 181 is connected to the laser applicator 182. The depth detecting unit 172 is adapted to detect a depth of an ablation applied to the sternum 22 by the cut laser beam 15.

Figure 6:
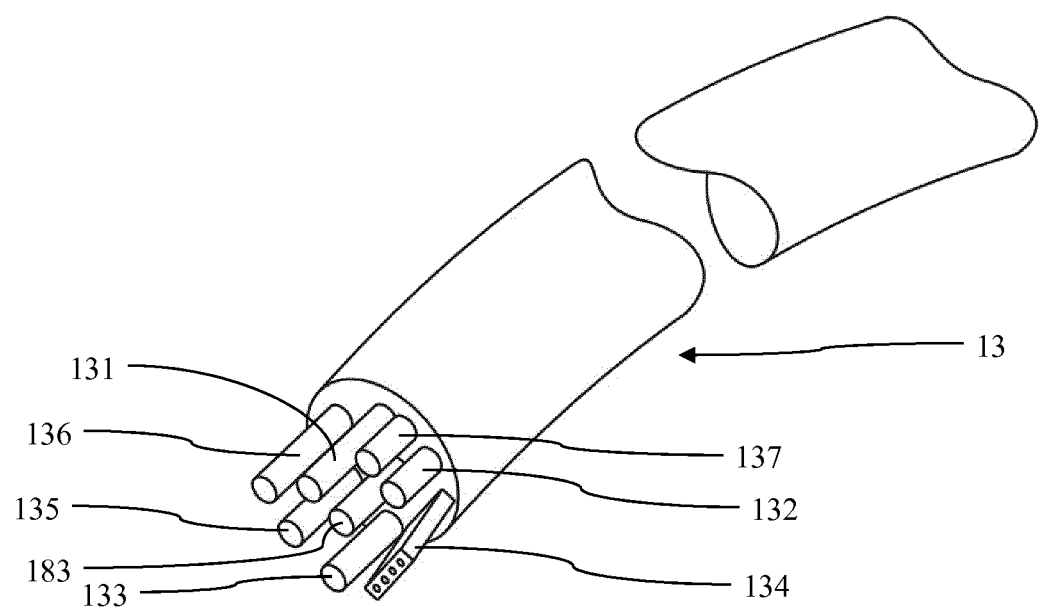
FIG. 6 shows a perspective view of a media wiring of the cutting device of FIG. 1.

As shown in FIG. 6 the media wiring 13 comprises a forward cooling media tube 131, a backward cooling media tube 132, a gas tube 133, power supply cables 134, a depth control optical fiber 135 of the depth detecting unit 172, a liquid tube 136 and a controller cable 137. It further houses an ablation optical fiber 183 of the laser device 18.

The power supply cables 134 are connected to all power consumers remote from the electronic unit 17. Thereby, the power consumers such as, in particular, the motors of the drive unit, the cameras 141, the suction nose and the parabolic mirror arrangement 16 are supplied with electric energy via the power supply cables 134 of the media wiring 13.

The forward cooling media tube 131 and the backward cooling media tube 132 are connected to a cooling entity. The cooling medium can be any liquid or other medium such as a sole suitable for cooling the attached components such as the laser source or the like. More particularly, in the forward cooling media tube 131 the cooling medium is provided from a cooling medium reservoir to the cooling entity and in the backward cooling media tube 132 the heated cooling medium is provided back after circulating through the cooling entity.

The gas tube 133 and the liquid tube 136 are connected to a nozzle body (not shown in the Figs.) near or at the laser source or parabolic mirror member 16. The nozzle body comprises plural two-fluid nozzles directed to the cut laser beam 15—sternum 22 contact area. By the two-fluid nozzles the liquid provided by the liquid tube 136 such as, e.g., sterile sodium chloride or distilled water, which can be enriched with an antiseptic substance, and the gas provided by the gas tube 133 are mixed at an elevated pressure in order to generate a spray. During ablation of the bone tissue of the sternum 22 the two-fluid nozzles spray to the cut laser beam 15—sternum 22 contact area for cooling and thereby minimizing heat transfer in the bone tissue. For example, the two-fluid nozzles can deliver the sterile sodium chloride at a flow rate of about 8 to 10 ml/min under a pressure of about 3 bar. The liquid is then removed from the sternum 22 together with the debris via the suction nose.

The controller cable 137 is connected to the processing unit and the controllable components of the cutting device 1 such as the motors of the drive unit, the cameras 141, the autofocusing arrangement, the two-fluid nozzles of the nozzle body and the like. Through the controller cable 137 the processing unit 173 communicates with the mentioned controllable components. For example, the processing unit 173 automatically adjusts the orientation of the lenses of the autofocusing unit considering the depth of the ablation of the bone tissue at the cut geometry of the sternum 22.

Figure 7:
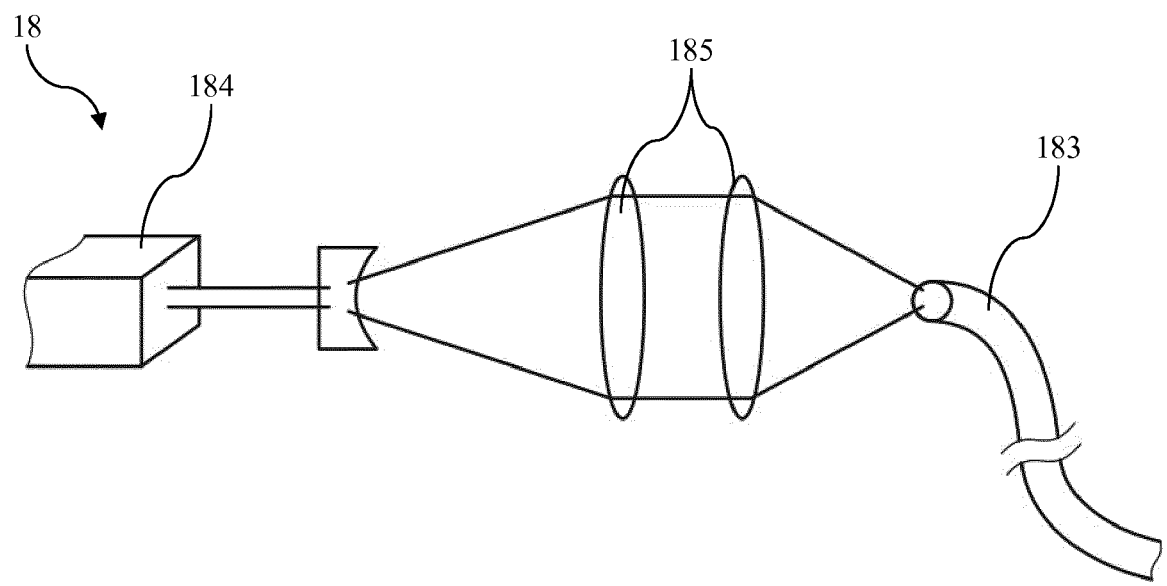
FIG. 7 shows a detail of a laser source of the cutting device of FIG. 1.

As can be seen in FIG. 4 together with FIG. 7, through the ablation optical fiber 183 the light of the cut laser beam 15 is provided from the Er:YAG laser 181 to the laser applicator 182 via its fiber connector 1821. For this, a laser beam generated by the laser 181 is introduced into the ablation optical fiber 183 as shown in FIG. 4. In particular, the Er:YAG laser 181 of the laser device 18 has a beam generator 184. An initial laser beam exits the beam generator 184 and is directed by focusing lenses 185 of the laser device 18 into the ablation optical fiber 183. There, it travels to and exits the laser source as described above.

Similarly as the laser beam for ablating the bone tissue a second laser beam is provided through the depth control optical fiber 135. This second laser beam is for detecting the depth of the ablation process on the sternum 2.

In use, the cutting device 1 can be applied in an embodiment of a method of cutting the sternum 22. Before the device 1 is used the sternum 22 is prepared in order to be accessible to the cutting device 1. For preparing the sternum 22 some steps can be applied preoperatively. For example, data about the sternum 22 can be obtained by computer tomography. The data can be analysed and on the computer tomography image an osteotomic geometry such as a sinusoidal line or curve can be defined on the sternum 22. Then the sternum 22 can be made accessible and the cutting device 1 can be fixed to the rib cage 2 such that the laser source is in the predefined position.

For ablating bone tissue at the sternum 22, the processing unit 173 controls the drive unit such that it moves the laser source together with the nozzle body over the sternum 22 along the cut geometry. Thereby, the sub-microsecond pulsed laser beam generated by the laser device of the cutting device 1 creates a line of adjacent circular spots. Since the spots are created alternatingly the bone tissue has time to cool down which allows for minimizing collateral damages to the bone tissue.

In order to efficiently ablate the bone tissue at the sternum 22, the cut laser beam 15 generated by the laser source is adjusted to have a wavelength of 2,940 nm. During delivery of the cut laser beam 15 to the sternum 22 a sterile sodium chloride is sprayed by the two-fluid nozzles in the nozzle body. Like this, the cut laser beam 15—sternum 22 contact area is cooled and hydrated.

During ablation the depth detecting unit 172 monitors and controls the depth of the ablated bone tissue. The cut laser beam 15 is adjusted to the depth such that bone tissue is precisely ablated from sternum 22 along the cut geometry.

Figure 8:
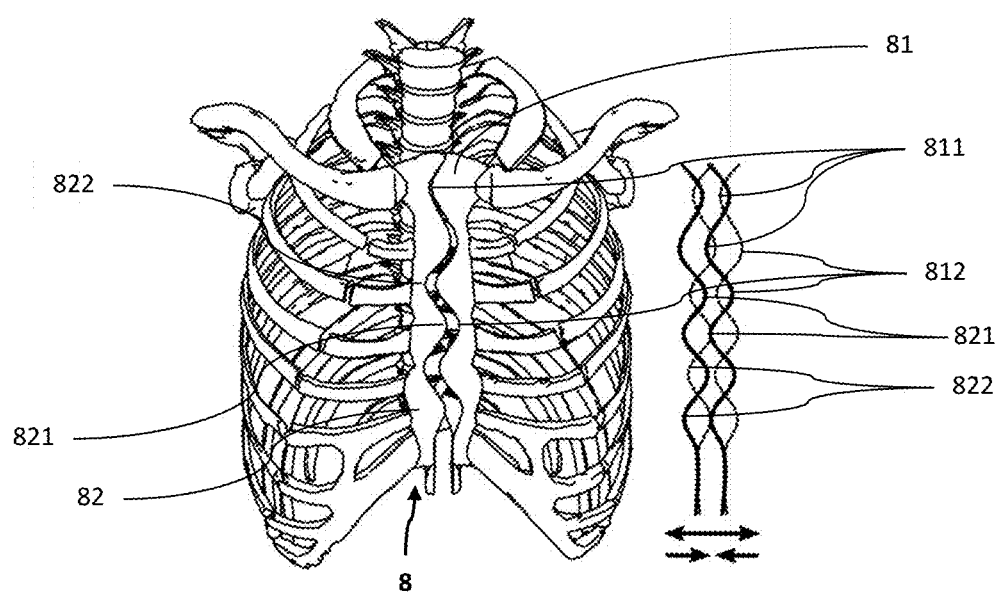
FIG. 8 shows a perspective view of a sophisticated cut geometry for cutting a sternum apart.

FIG. 8 shows an example of a sophisticated cut geometry which can be provided by a cutting device according to the invention in a sternum opening surgery process. A sternum 8 is cut along the cut geometry with a twisted structure into a right-hand first sternum portion 81 and a left-hand second sternum portion 82. The structure of the cut geometry is defined by a periodic sinus function with a non-uniform period generating plural non-uniform projections 811 and recesses 812 at the first sternum portion 81 and corresponding plural non-uniform projections 821 and recesses 822 at the second sternum portion 82. In addition thereto, the sinusoidal function varies in a proximal or interior direction of the sternum 8 such that a non-perpendicular respective cutting angle is formed. Using such a non-periodic cutting function and a twisted cutting surface for opening the sternum 8 can guarantee that the chest is closed again at the original position. Thus, the cut geometry only allows a distinct reassembling of the first sternum portion 81 and the second sternum portion 82 into a predefined target situation which is equal to the initial situation.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively.

The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A cutting device for cutting a sternum of a patient, comprising:
   a laser source adapted to generate a cut laser beam;
   a drive unit having a beam adjusting structure for directing the cut laser beam generated by the laser source along a predefined cut geometry at the sternum;
   a support carrying the laser source; and
   a correction arrangement, wherein:
   the support has a carrier element configured to mount the laser source, and has a mounting structure adapted to be fixed to the carrier element, wherein the mounting structure is adapted to be fixed to a rib cage of the patient such that the laser source is in a predefined position with respect to the sternum and such that the laser source moves together with the rib cage during movement of the patient's ribs,
   the laser source is movably connected to the carrier element, and the drive unit is configured to move the laser source relative to the carrier element;
   the correction arrangement comprises a sensor mounted on the carrier element and directed to the sternum, wherein the sensor is adapted to provide a spatial signal related to a position of the cut laser beam of the laser source relative to the sternum and related to movement of the carrier element relative to the sternum,
   the correction arrangement further includes a computing unit adapted to: automatically identify, based on the spatial signal from the sensor, a movement of the laser source relative to the sternum that is causing the cut laser beam of the laser source to deviate from the predefined cut geometry and automatically output a control signal to the drive unit to adjust a position of the laser source relative to the sternum to correct deviation of the cut laser beam of the laser source with respect to the predefined cut geometry.

2. The cutting device according to claim 1, wherein the support comprises a laser mount to which the laser source is fixedly mounted, and wherein the laser mount is movably connected to the carrier element.

3. The cutting device according to claim 2, wherein the drive unit is adapted to move the laser mount relative to the carrier element.

4. The cutting device according claim 3, wherein the drive unit comprises a linear motor adapted to move the laser mount relative to the carrier element.

5. The cutting device according to claim 3, wherein the drive unit comprises a beam director adapted to adjust a direction into which the cut laser beam generated by the laser source is provided.

6. The cutting device according to claim 5, wherein the beam director comprises an adjustable optics adapted to redirect the cut laser beam generated by the laser source.

7. The cutting device according to claim 1, wherein the mounting structure of the support comprises a plurality of legs each having a foot shaped to be fixed to a rib of the rib cage.

8. The cutting device according to claim 1, wherein the mounting structure of the support comprises a belt adapted to fix the mounting structure to the rib cage.

9. The cutting device according to claim 1, further comprising a debris extraction unit adapted to evacuate debris generated by the cut laser beam hitting the sternum.

10. The cutting device according to claim 1, further comprising a depth detecting unit adapted to detect a depth of an ablation applied to the sternum by the cutting device.

11. The cutting device according to claim 1, further comprising an auto-focusing arrangement adapted to automatically adjust a focus of the cut laser beam in relation to the sternum.

12. The cutting device according to claim 1, further comprising a depth control unit arranged to stop the laser source from generating the cut laser beam when the sternum is cut to a predefined extent.

13. The cutting device according to claim 12, wherein the depth control unit comprises a laser based optical coherence tomography device.

14. The cutting device according to claim 12, wherein the depth control unit comprises a laser based photo-acoustic spectroscopy sensor.

15. The cutting device according to claim 1, wherein the sensor includes the distance laser source, and wherein the distance laser source is configured to conceive a distance laser beam from the sternum.

16. The cutting device according to claim 1, wherein the sensor includes the ultrasonic sensor, and wherein an ultrasonic sensor is configured to conceive an acoustic wave from the sternum.

17. The cutting device according to claim 1, wherein the sensor includes an infrared sensor, and wherein the infrared sensor is configured to conceive infrared light from the sternum.

* * * * *